US012714679B2

(12) United States Patent
Krishna et al.

(10) Patent No.: US 12,714,679 B2

(45) Date of Patent: Aug. 25, 2026

(54) FULLERENES TO TREAT DISEASES AND CONDITIONS

(71) Applicant: The Cleveland Clinic Foundation, Cleveland, OH (US)

(72) Inventors: Vijay Krishna, Beachwood, OH (US); Christopher Hine, Shaker Heights, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 0 days.

(21) Appl. No.: 18/409,328

(22) Filed: Jan. 10, 2024

(65) Prior Publication Data

US 2024/0139121 A1 May 2, 2024

Related U.S. Application Data

(62) Division of application No. 17/277,099, filed as application No. PCT/US2019/052682 on Sep. 24, 2019, now abandoned.

(60) Provisional application No. 62/735,621, filed on Sep. 24, 2018.

(51) Int. Cl.

| | |
|---|---|
| ***A61K 31/047*** | (2006.01) |
| ***A23L 33/00*** | (2016.01) |
| ***A23L 33/115*** | (2016.01) |
| ***A23L 33/125*** | (2016.01) |
| ***A23L 33/18*** | (2016.01) |

(52) U.S. Cl.

CPC .......... *A61K 31/047* (2013.01); *A23L 33/115* (2016.08); *A23L 33/125* (2016.08); *A23L 33/18* (2016.08); *A23L 33/30* (2016.08)

(58) Field of Classification Search

CPC ............................ A61K 31/045; A61K 31/047

See application file for complete search history.

(56) References Cited

U.S. PATENT DOCUMENTS

| | | | | |
|---|---|---|---|---|
| 5,648,523 | A | 7/1997 | Chiang | |
| 6,833,145 | B1 | 12/2004 | Hirata et al. | |
| 9,567,439 | B1 * | 2/2017 | Pyun | C08G 75/16 |
| 9,950,977 | B2 | 4/2018 | Krishna et al. | |
| 2011/0165216 | A1 | 7/2011 | Chen et al. | |
| 2016/0331698 | A1 | 11/2016 | Sugaya et al. | |
| 2017/0056334 | A1 | 3/2017 | Petyaev | |

FOREIGN PATENT DOCUMENTS

| | | |
|---|---|---|
| CN | 108497099 | 9/2018 |
| WO | WO 2018/033033 | 2/2018 |
| WO | WO 2019/184419 | 10/2019 |

OTHER PUBLICATIONS

Miranda et al., "Characterization of fundamental catalytic properties of MoS2/WS2 nanotubes and nanoclusters for desulfurization catalysis—a surface chemistry study", 2012, U.S. Department of Energy, pp. 1-11 (Year: 2012).*

Taylor, "Surprises, Serendipity, and Symmetry in Fullerene Chemistry", 2000, Synlett, 6, pp. 776-793 (Year: 2000).*

International Search Report and Written Opinion. Mailed Dec. 12, 2019. 10 pages.

Alves et al., Sodium hydrosulfide improves the protective potential of the cardioplegic histidine buffer solution. Eur J Pharmacol. Mar. 1, 2011;654(1):60-7.

Blackstone et al., H2S induces a suspended animation-like state in mice. Science. Apr. 22, 2005;308(5721):518.

Darwish et al., The c60-Catalysed Oxidation of Hydrogen Sulphide to Sulphur. Fullerene Science & Technology, 1993. 1(4), 571-574.

Elrod et al., Hydrogen sulfide attenuates myocardial ischemia-reperfusion injury by preservation of mitochondrial function. Proc Natl Acad Sci U S A. Sep. 25, 2007;104(39):15560-5.

Giuliani et al., Hydrogen sulfide slows down progression of experimental Alzheimer's disease by targeting multiple pathophysiological mechanisms. Neurobiol Learn Mem. Sep. 2013;104:82-91.

Hine et al., Endpoint or Kinetic Measurement of Hydrogen Sulfide Production Capacity in Tissue Extracts. Bio Protoc. Jul. 5, 2017;7(13):e2382. 18 pages.

Hine et al., Endogenous hydrogen sulfide production is essential for dietary restriction benefits. Cell. Jan. 15, 2015;160(1-2):132-44.

Hine et al. Hypothalamic-Pituitary Axis Regulates Hydrogen Sulfide Production. Cell Metab. Jun. 6, 2017;25(6):1320-1333.e5.

Huang et al., Down-regulated CBS/H2S pathway is involved in high-salt- induced hypertension in Dahl rats. Nitric Oxide. Apr. 3, 20150;46:192-203.

Jha et al., Hydrogen sulfide attenuates hepatic ischemia-reperfusion injury: role of antioxidant and antiapoptotic signaling. Am J Physiol Heart Circ Physiol. Aug. 2008;295(2):H801-6.

Kovacic et al., Total plasma sulfide in congestive heart failure. J Card Fail. Jul. 2012;18(7):541-8.

Liu et al., Hydrogen sulfide maintains mesenchymal stem cell function and bone homeostasis via regulation of Ca(2+) channel sulfhydration. Cell Stem Cell. Jul. 3, 2014;15(1):66-78.

Paul et al., Cystathionine γ-lyase deficiency mediates neurodegeneration in Huntington's disease. Nature. May 1, 2014;509(7498):96-100.

Polhemus et al., A novel hydrogen sulfide prodrug, SG1002, promotes hydrogen sulfide and nitric oxide bioavailability in heart failure patients. Cardiovasc Ther. Aug. 2015;33(4):216-26.

Sponholz et al., Polymorphisms of cystathionine beta-synthase gene are associated with susceptibility to sepsis. Eur J Hum Genet. Jul. 2016;24(7):1041-8.

Suzuki et al., Hydrogen sulfide replacement therapy protects the vascular endothelium in hyperglycemia by preserving mitochondrial function. Proc Natl Acad Sci U S A. Aug. 16, 2011;108(33):13829-34.

(Continued)

*Primary Examiner* — Brenda L Coleman
*Assistant Examiner* — Madeline E Braun
(74) *Attorney, Agent, or Firm* — Casimir Jones, SC; Jason R. Bond

(57) ABSTRACT

Provided herein are compositions, systems, kits, and methods for treating a subject with a disease or condition by administering a composition comprising fullerenes to the subject such that H2S is generated in the subject. In certain embodiments, the disease or condition is associated with inflammation and/or below normal H2S levels. In certain embodiments, the fullerenes are polyhydroxy fullerenes (PHFs).

2 Claims, 10 Drawing Sheets

(56) References Cited

OTHER PUBLICATIONS

Szabo. Roles of hydrogen sulfide in the pathogenesis of diabetes mellitus and its complications. Antioxid Redox Signal. Jul. 1, 2012;17(1):68-80.

Xue et al., Hydrogen sulfide treatment promotes glucose uptake by increasing insulin receptor sensitivity and ameliorates kidney lesions in type 2 diabetes. Antioxid Redox Signal. Jul. 1, 2013;19(1):5-23.

Yang et al., H2S as a physiologic vasorelaxant: hypertension in mice with deletion of cystathionine gamma-lyase. Science. Oct. 24, 2008;322(5901):587-90.

Zhang et al., Hydrogen sulfide, the next potent preventive and therapeutic agent in aging and age-associated diseases. Mol Cell Biol. Mar. 2013;33(6):1104-13.

Zhao et al., The vasorelaxant effect of H(2)S as a novel endogenous gaseous K(ATP) channel opener. Embo J. Nov. 1, 2001;20(21):6008-16.

Zhu et al., Kinetic properties of polymorphic variants and pathogenic mutants in human cystathionine gamma-lyase. Biochemistry. Jun. 10, 2008;47(23):6226-32.

* cited by examiner

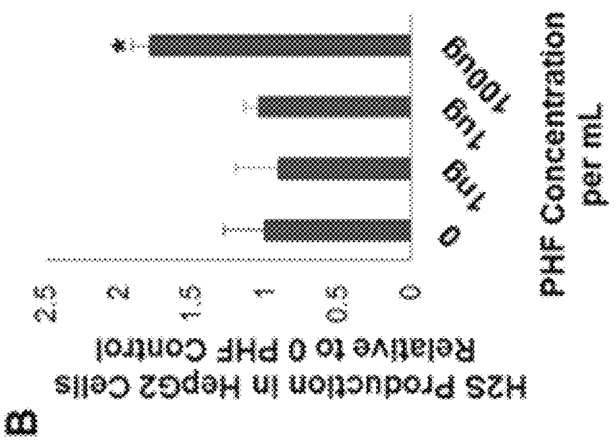
FIG. 1
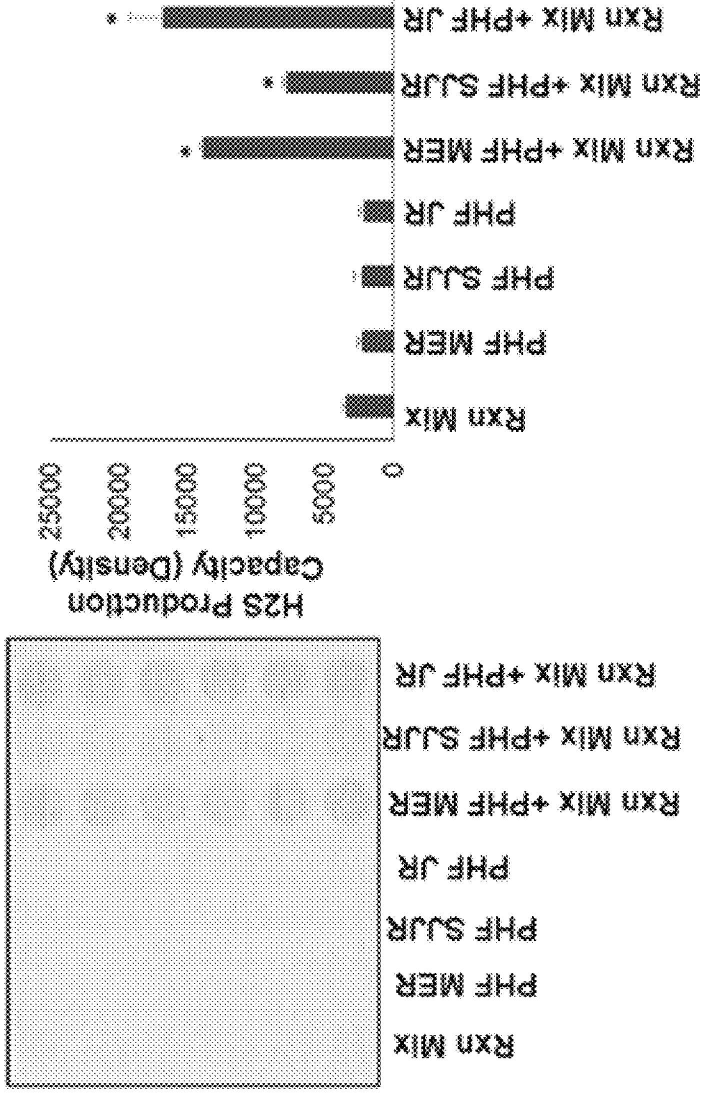

PHF + PLP
PHF
$H_2S$ Concentration (mM)
0.1
0.01
0.001
0
0
10
20
30
40
50
60
70
Temperature (°C)

PHF + PLP
PHF
$H_2S$ Concentration (mM)
0.1
0.01
0.001
3
4
5
6
7
8
9
10
pH

A

B

FULLERENES TO TREAT DISEASES AND CONDITIONS

The present application is a division of U.S. patent application Ser. No. 17/277,099, filed Mar. 17, 2021, which is a 371 of International Application PCT/US2019/052682, filed Sep. 24, 2019, which claims priority to U.S. Provisional Application Ser. No. 62/735,621, filed Sep. 24, 2018, herein incorporated by reference in its entirety.

FIELD

Provided herein are compositions, systems, kits, and methods for treating a subject with a disease or condition by administering a composition comprising fullerenes to the subject such that H2S is generated in said subject. In certain embodiments, the disease or condition is associated with inflammation and/or below normal H2S levels. In certain embodiments, the fullerenes are polyhydroxy fullerenes (PHFs).

BACKGROUND

Within the past decade, it has become apparent that hydrogen sulfide ($H_2S$) gas plays a strong role in aging and health (Hine et al., 2017; Zhang et al., 2013). H2S is a signaling molecule with multitude of biological functions and is produced from cysteine by the enzymes cystathionine β-synthase (CBS) and cystathionine γ-lyase (CGL). Reduction in production levels of endogenous H2S has been implicated in many diseases including aging (Huang et al., 2015; Yang et al., 2008), cardiovascular (Kovacic et al., 2012), metabolic (Szabo, 2012) (Liu et al., 2014) and neurodegenerative disorders (Paul et al., 2014). Exposure to supra-physiological levels of H2S can be beneficial. For example, in rodents H2S increases vasodilation of blood vessels and lowers blood pressure (Zhao et al., 2001), protects against ischemia reperfusion injury to multiple organs including heart (Elrod et al., 2007) and liver (Jha et al., 2008), improves insulin sensitivity and/or responses to glucose (Suzuki et al., 2011; Xue et al., 2013), delays cognitive decline in animal models of Alzheimer's disease (Giuliani et al., 2013), and is associated or causative of extended longevity (Hine et al., 2015).

Exogenous H2S supplementation is conceptually the most straightforward, with multiple different forms of H2S already available, from the short-acting gas itself (Blackstone et al., 2005) to short- and long-lasting chemical H2S donors (Alves et al., 2011; Polhemus et al., 2015). However, due to the gas and donors being highly reactive, this approach risks acute toxicity, so that targeted delivery to the proper organ and cell type at the optimal dose may be challenging to achieve. Two of the most potent mechanisms to boost endogenous enzymatic H2S production for beneficial endpoints is via dietary restriction (Hine et al., 2015) and lowering of growth hormone and thyroid hormone signaling via dietary, pharmacological, or genetic means (Hine et al., 2017). However, the translatability of these two interventions to boost H2S in humans is poor, as patient compliance and safety issues prevent them from being widely implemented. Additionally, mutations or epigenetic gene-silencing present in the human population for CBS (Sponholz et al., 2016) or CGL (Zhu et al., 2008) that result in impaired enzymatic activity would negate these types of interventions.

SUMMARY

Provided herein are compositions, systems, kits, and methods for treating a subject with a disease or condition by administering a composition comprising fullerenes to the subject such that H2S is generated in said subject. In certain embodiments, the disease or condition is associated with inflammation and/or below normal H2S levels. In certain embodiments, the fullerenes are polyhydroxy fullerenes (PHFs).

In some embodiments, provided herein are methods of treating a subject with a disease or condition comprising: administering a composition comprising fullerenes to said subject with said disease or condition (e.g., such that H2S is generated in said subject). In certain embodiments, the disease or condition is associated with inflammation and/or below normal H2S levels in said subject. In further embodiments, the administering reduces or eliminates at least one symptom of said disease or condition.

In some embodiments, the fullerenes comprise polyhydroxy fullerenes. In certain embodiments, the fullerenes in said composition are all one type of fullerene. In further embodiments, the fullerenes in the composition are two or more types of fullerenes. In other embodiments, the fullerenes in the composition are all one type of fullerene selected from the group consisting of: $C_{60}(OH)_9O_7Na_6$; $C_{60}(OH)_{11}O_8Na_5$; $C_{60}(OH)_{11}O_{12}Na_8$; $C_{60}(OH)_{11}O_{20}Na_{10}K_6$; $C_{60}(OH)_6 O_4Na_4$; $C_{60}(OH)_{20}O_8Na_4$; $C_{60}(OH)_{10}O_{13}Na_6$; $C_{60}(OH)_4 O_{14}Na_{17}$; $C_{60}(OH)_{13}O_4Na_3$; $C_{60}(OH)_{10}$; $C_{60}(OH)_{22-24}$; $C_{60}(OH)_{36}$; $C_{60}(OH)_{44}$; $C_{60}O_{13}Na_{14}$; $Gd@C_{82}(OH)_{15}O_{12}Na_5$; $Gd_3N@C_{80}(OH)_{13}O_9Na_6$; $C_{60}(OH)_{11}O_8S_8Na_5$; $C_{60}(OH)_{11}(SH)_5O_{81}Na_5$; $C_{60}C_{12}N_4H_{24}$; and $C_{60}C_{12}N_6H_{30}O_{12}$. In other embodiments, the fullerenes in said composition are two or more types of fullerenes selected from the group consisting of: $C_{60}(OH)_9O_7Na_6$; $C_{60}(OH)_{11}O_{81}Na_8$; $C_{60}(OH)_{11}O_{12}Na_8$; $C_{60}(OH)_{11}O_{20}Na_{10}K_6$; $C_{60}(OH)_6O_4Na_4$; $C_{60}(OH)_{20}O_8Na_4$; $C_{60}(OH)_{10}O_{13}Na_6$; $C_{60}(OH)_4O_{14}Na_{17}$; $C_{60}(OH)_{13}O_4Na_3$; $C_{60}(OH)_{10}$; $C_{60}(OH)_{22-24}$; $C_{60}(OH)_{36}$; $C_{60}(OH)_{44}$; $C_{60}O_{13}Na_{14}$; $Gd@C_{82}(OH)_{15}O_{12}Na_5$; $Gd_3N@C_{80}(OH)_{13}O_9Na_6$; $C_{60}(OH)_{11}O_8S_8Na_5$; $C_{60}(OH)_{11}(SH)_5O_8Na_5$; $C_{60}C_{12}N_4H_{24}$; and $C_{60}C_{12}N_6H_{30}O_{12}$. In certain embodiments, the fullerenes are one or more compounds according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide or actinide, n is a number ranging from 10 to 270; and t, u, v, w, x, y and z can range from 0 to the total number of carbon atoms present in the cage.

In particular embodiments, the composition comprises a food product. In certain embodiments, the food product comprises carbohydrates, proteins, and fats. In other embodiments, the food product is in a form selected from the group consisting of: mayonnaise, margarine, low fat spread, yoghurt, a fruit smoothie, a beverage, a protein smoothie, a cheese spread, processed cheese, a dairy dessert, a flavored milk, cream, a fermented milk product, cheese, butter, a condensed milk product, an ice cream mix, a soy product, pasteurized liquid egg, a bakery product, a confectionary product, confectionary bar, chocolate bar, high fat bar, energy bar, liquid emulsion, powder, spray dried powder, freeze dried powder, pudding, a gel, a gel concentrate, a liquid drink, and jelly. In certain embodiments, said composition is located in a skin patch or eye drop solution.

In some embodiments, provided herein are methods of comprising: contacting a sulfur-containing compound or thiol-containing compound, with a composition comprising fullerenes in vitro such that H2S is generated. In certain embodiments, the methods further comprise capturing at least some of said H2S that is generated. In additional embodiments, the capture H2S is stored. In certain embodiments, the fullerenes are used in various biotechnology methods for processing amino acids.

In some embodiments, provided herein are compositions or articles of manufacture comprising: a food product, wherein said food product comprises a composition comprising fullerenes. In additional embodiments, the food product comprises carbohydrates, proteins, and fats. In further embodiments, the food product is in a form selected from the group consisting of: mayonnaise, margarine, low fat spread, yoghurt, a fruit smoothie, a protein smoothie, a cheese spread, processed cheese, a dairy dessert, a flavored milk, cream, a fermented milk product, cheese, butter, a condensed milk product, an ice cream mix, a soy product, pasteurized liquid egg, a bakery product, a confectionary product, confectionary bar, chocolate bar, high fat bar, energy bar, liquid emulsion, powder, spray dried powder, freeze dried powder, pudding, a gel, a gel concentrate, a liquid drink, and jelly. In certain embodiments, the food product qualifies as a medical food as defined in the Orphan Drug Act.

In certain embodiments, the fullerenes in the food product comprise polyhydroxy fullerenes. In additional embodiments, the fullerenes in said food product are all one type of fullerene. In other embodiments, the fullerenes in the food production are two or more types of fullerenes. In some embodiments, the fullerenes in the food product are all one type of fullerene selected from the group consisting of: $C_{60}(OH)_9O_7Na_6$; $C_{60}(OH)_{11}O_8Na_5$; $C_{60}(OH)_{11}O_{12}Na_8$; $C_{60}(OH)_{11}O_{20}Na_{10}K_6$; $C_{60}(OH)_6O_4Na_4$; $C_{60}(OH)_{20}O_8Na_4$; $C_{60}(OH)_{10}O_{13}Na_6$; $C_{60}(OH)_4O_{14}Na_{17}$; $C_{60}(OH)_{13}O_4Na_3$; $C_{60}(OH)_{10}$; $C_{60}(OH)_{22\text{-}24}$; $C_{60}(OH)_{36}$; $C_{60}(OH)_{44}$; $C_{60}O_{13}Na_{14}$; $Gd@C_{82}(OH)_{15}O_{12}Na_5$; $Gd_3N@C_{80}(OH)_{13}O_9Na_6$; $C_{60}(OH)_{11}O_8S_8Na_5$; $C_{60}(OH)_{11}(SH)_5O_8Na_5$; $C_{60}C_{12}N_4H_{24}$; and $C_{60}C_{12}N_6H_{30}O_{12}$. In other embodiments, the fullerenes in the food product are two or more types of fullerenes selected from the group consisting of: $C_{60}(OH)_9O_7Na_6$; $C_{60}(OH)_{11}O_8Na_5$; $C_{60}(OH)_{11}O_{12}Na_8$; $C_{60}(OH)_{11}O_{20}Na_{10}K_6$; $C_{60}(OH)_6O_4Na_4$; $C_{60}(OH)_{20}O_8Na_4$; $C_{60}(OH)_{10}O_{13}Na_6$; $C_{60}(OH)_4O_{14}Na_{17}$; $C_{60}(OH)_{13}O_4Na_3$; $C_{60}(OH)_{10}$; $C_{60}(OH)_{22\text{-}24}$; $C_{60}(OH)_{36}$; $C_{60}(OH)_{44}$; $C_{60}O_{13}Na_{14}$; $Gd@C_{82}(OH)_{15}O_{12}Na_5$; $Gd_3N@C_{80}(OH)_{13}O_9Na_6$; $C_{60}(OH)_{11}O_8S_8Na_5$; $C_{60}(OH)_{11}(SH)_5O_8Na_5$; $C_{60}C_{12}N_4H_{24}$; and $C_{60}C_{12}N_6H_{30}O_{12}$.

DESCRIPTION OF THE FIGURES

FIG. 1: Polyhydroxy fullerenes (PHF) catalytically produces hydrogen sulfide (H2S). Panel A) Different PHF formulations MER, SJJR, and JR stimulate H2S production catalytically in a cell free chemical reaction involving cysteine and vitamin B6 as determined by the lead acetate/lead sulfide method (left image) and quantified in the graph to the right. * indicates significant difference ($p<0.05$) compared to reaction (Rxn) mix control using Student's T-test. Panel B) PHF dose-dependently boosts endogenous H2S production in human liver derived (HepG2) cells as determined by an increase in the fluorescence of an H2S detecting chemical probe. * indicates significant difference ($p<0.05$) compared to 0 PHF control group using Student's T-test.

FIGS. 4A-D: Catalytic properties of PHF. FIG. 4A) Effect of PHF concentration on H2S production from cysteine (initial concentration of 40 mM) in the presence or absence of pyridoxal-5'-phosphate (PLP). FIG. 4B) Confirmation of PHF's role as a catalyst. Every 24 hours, 10 mM of cysteine was added, whereas PHF was not replenished. The absence of decline in H2S production indicates that PHF is a catalyst and not a reactant. No further additions of cysteine were made after day 17. FIG. 4C) and FIG. 4D) Effect of temperature (C) and pH (D) on catalytic production of H2S with PHF in presence and absence of PLP. PLP (when added) initial concentration was 1 mM; PHF concentration (except for panel A) was 10 mg/mL.

DEFINITIONS

Figure 2:
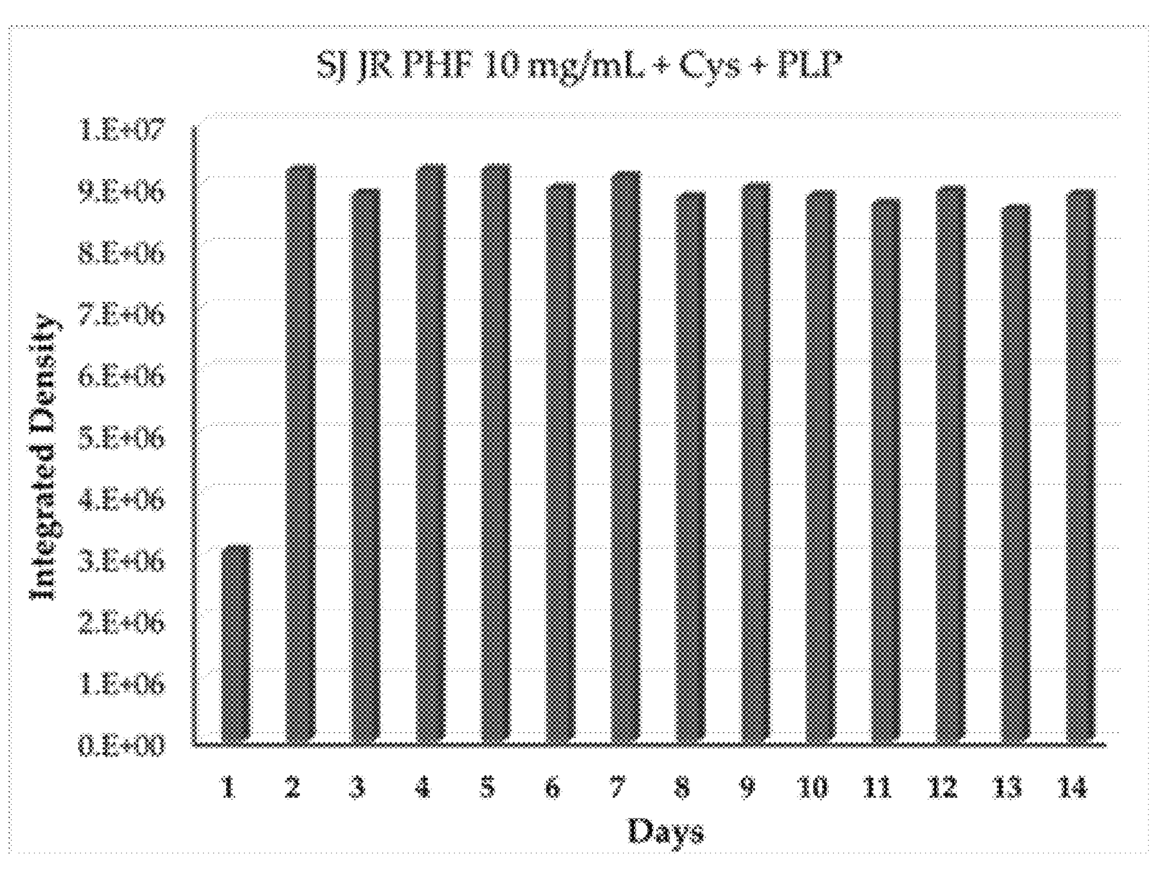
FIG. 2. Catalytic production of H2S: PHF (SJJR; 10 mg/mL) was added to a mixture of L-cysteine (10 mM) and pyridoxal L-phosphate (PLP; 1 mM) in a 96-well plate and then covered with a blotting paper saturated with lead acetate. After 24 hours, the lead acetate paper was removed and scanned. The lead sulfide dots were analyzed for average integrated density using ImageJ. After every 24 hours, the wells were replenished with L-cysteine (10 mM) and covered with the lead acetate paper and the lead sulfide dots were analyzed. The figure shows that the H2S production does not decrease with time showing that PHF is not consumed and hence, PHF is a catalyst.
Figure 3:
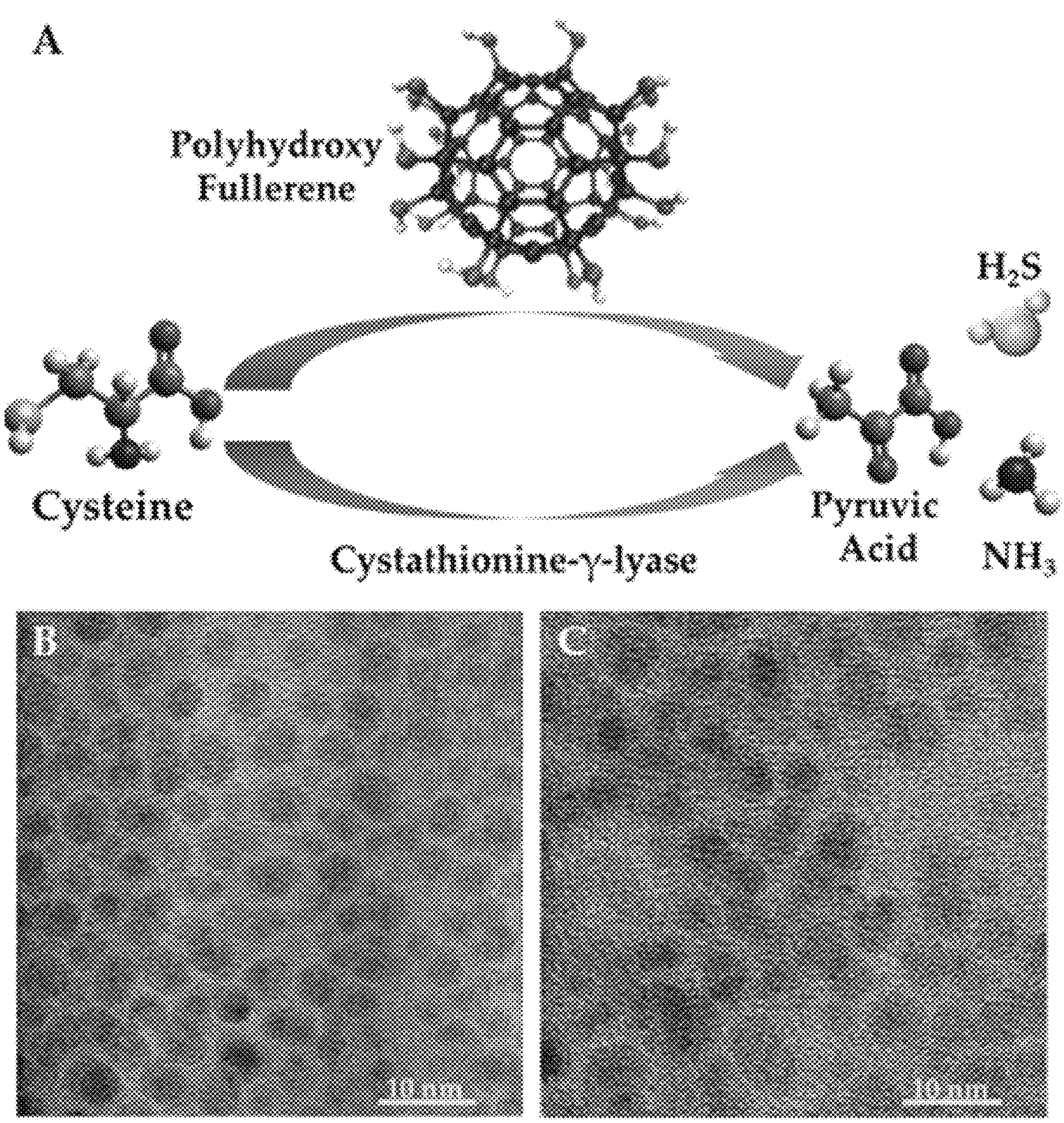
FIG. 3: Panel A) a hypothetical schematic illustration of the breakdown of cysteine to hydrogen sulfide, ammonia and pyruvic acid. While the present disclosure is not limited to any particular mechanism and an understanding of the mechanism is not necessary to practice the invention, it is believed that polyhydroxy fullerenes (PHF) mimic carbon-sulfur lyases. It was found during work conducted during development of embodiments herein that PHFs catalyze the breakdown of cysteine under physiological conditions. Panel B) HR-TEM image of PHF ($C_{60}(OH)_9O_7Na_6$) showing a cluster size of 3.4±0.5 nm. Panel C) HR-TEM image of CGL showing a molecular size of 4.1±0.4 nm.

To facilitate an understanding of the present technology, a number of terms and phrases are defined below. Additional definitions are set forth throughout the detailed description.

Throughout the specification and claims, the following terms take the meanings explicitly associated herein, unless the context clearly dictates otherwise. The phrase "in one embodiment" as used herein does not necessarily refer to the same embodiment, though it may. Furthermore, the phrase "in another embodiment" as used herein does not necessarily refer to a different embodiment, although it may. Thus, as described below, various embodiments of the technology may be readily combined, without departing from the scope or spirit of the technology.

In addition, as used herein, the term "or" is an inclusive "or" operator and is equivalent to the term "and/or" unless the context clearly dictates otherwise. In addition, throughout the specification, the meaning of "a", "an", and "the" include plural references. The meaning of "in" includes "in" and "on."

The term "medical food," as used herein, is as defined by the Orphan Drug Act (21 U.S.C. 360ee(b)(3)) of 1988, which is "a food which is formulated to be consumed or administered enterally under the supervision of a physician and which is intended for the specific dietary management of a disease or condition for which distinctive nutritional requirements, based on recognized scientific principles, are established by medical evaluation."

As used herein, the terms "subject" and "patient" refer to any animal, such as a mammal like a dog, cat, bird, livestock, and preferably a human (e.g., a human with a disease such as asthma, a fibrotic disease, obesity, etc.).

As used herein, the term "administration" refers to the act of giving a drug, prodrug, or other agent (e.g., food product), or therapeutic treatment to a subject. Exemplary routes of administration to the human body can be through the mouth (oral), skin (transdermal, topical), nose (nasal), lungs (inhalant), oral mucosa (buccal), by injection (e.g., intravenously, subcutaneously, intratumorally, intraocular, intraperitoneally, etc.), and the like.

As used herein, "fullerene" refers a general class of molecules that exists essentially in the shape of a three dimensional polyhedron containing from 20 to 1500 carbon atoms, and which comprises carbon atoms as the predominant element from which they are composed. The fullerenes include but are not limited to C-28, C-32, C-44, C-50, C-58, C-60, C-70, C-84, C-94, C-250 and C-540. According to this nomenclature, the fullerene which contains 60 carbon atoms is denoted C-60, the fullerene which contains 70 carbon atoms is denoted C-70, etc. Also included among the fullerenes are the substituted fullerenes. These are molecular fullerenes which have had one or more of the atoms which comprise the fullerene cage structure replaced by an atom other than carbon, such as nitrogen, boron or titanium, yet essentially retain the geometry of a polyhedron upon being so substituted. Also included among the fullerenes are endohedral fullerenes, in which atoms of elements other than carbon (e.g., iron, gadolinium and sulfur) reside inside the cage structure. Included in the term "fullerene" is a "functionalized fullerene" which refers to fullerene (CX where x is 20 to 1500) with side groups attached to the outer surface of the cage via covalent bonds, ionic bonds, or Dewar coordination, or Kubas interactions, or any combination thereof. The side groups can be either inorganic, including, but not exclusive to, OH, Br, $H_2$, Gd, Ti, organic, including, but not exclusive to, $C(COOH)_2$, or any combination of organic and/or inorganic functional groups. The number of functional groups attached per cage of fullerene can vary from 1 to a majority of the number of carbons in the fullerene cage. Functionalized fullerenes have different physical and chemical properties based on the type and number of side groups. In certain embodiments, the fullerenes herein are compounds according to the formula $C_{2n}(OH)_t(SH)_u(NH_2)_v(COOH)_w(COOM)_xO_yM_z$, wherein M is an alkali metal, alkaline earth metal, transition metal, post-transition metal, lanthanide or actinide, n is a number ranging from 10 to 270; t, u, v, w, x, y and z can range from 0 to the total number of carbon atoms present in the cage. Examples of fullerenes are found in U.S. Pat. No. 9,950,977, which is herein incorporated by reference, in its entirety, particularly for the fullerene compounds disclosed therein. In certain embodiments, the fullerenes employed herein are polyhydroxy fullerenes (PHFs).

DETAILED DESCRIPTION

Provided herein are compositions, systems, kits, and methods for treating a subject with a disease or condition by administering a composition comprising fullerenes to the subject such that H2S is generated in said subject. In certain embodiments, the disease or condition is associated with inflammation and/or below normal H2S levels. In certain embodiments, the fullerenes are polyhydroxy fullerenes (PHFs).

In work conducted during embodiments of the present disclosure, experiments suggest that PHF exposed to H2S is modified and becomes catalytically more active than just PHF. While the present disclosure is not limited to any particular mechanism, and an understanding of the mechanism is not necessary to practice the invention, it is believed that PHF has been modified with thiol groups. Such thiol-modified PHF's are contemplated as one type of fullerene to be used with the methods, compositions, kits, and systems described herein.

In work conducted during development of embodiments disclosed herein, it was determined that a carbon-based nanomaterial, polyhydroxy fullerenes (PHF) catalytically generates H2S from sulfur containing amino acids (e.g., cysteine) and enhances endogenous production of H2S. Hydrogen sulfide ($H_2S$) is a gaseous signaling molecule with multitude of biological functions. Reduced endogenous levels of H2S has been implicated in metabolic, cardiovascular, neurologic and immunologic diseases. In general, the H2S production depended on the concentration of PHF and type of sulfur-containing compound (e.g., amino acid). In certain embodiments, the catalytic activity of PHF and the endogenous H2S production rate is controlled by incorporating PHF in various matrices, such as inorganic, polymeric or metallic. Further, varying the size of the PHF-containing particles and distribution of PHF in matrices affect the catalytic activity and endogenous production rate. Work conducted during development of embodiments disclosed herein demonstrated that PHF catalytically generates H2S with amino acids (cysteine and homocysteine), and enhances endogenous production of H2S in liver cells. In certain embodiments, the fullerenes employed herein (e.g., PHFs) are pre-exposed to H2S gas or NaHS in liquid form. In this regard, such pre-exposed fullerenes may exhibit enhanced catalytic activity.

Table 1 below provides a comparison of steady state kinetic coefficients for PHF and CGL, with different substrates in presence and absence of PLP.

TABLE 1

| | Catalyst | Substrate | $K_m$ (mM) | $V_{max}$ (nM/s) | $K_{CAT}$ (/s) | $K_{CAT}/K_M$ (/Ms) |
|---|---|---|---|---|---|---|
| With PLP | CGL | L-Cysteine | 25.4 | 2.9 | $1.3 \times 10^2$ | 0.507 |
| | PHF | L-Cysteine | 26.4 | 9.1 | $6.7 \times 10^4$ | 0.023 |
| | PHF | D,L-Homocysteine | 62.3 | 1.7 | $1.3 \times 10^4$ | 0.002 |
| | PHF | N-Acetyl Cysteine | 144.1 | 0.6 | $4.4 \times 10^5$ | 0.0003 |
| Without PLP | CGL | L-Cysteine | 152.4 | 1.3 | $5.8 \times 10^3$ | 0.038 |
| | PHF | L-Cysteine | 28.1 | 5.3 | $3.9 \times 10^4$ | 0.014 |
| | PHF | D,L-Homocysteine | 99.3 | 1.1 | $8.1 \times 10^5$ | 0.0008 |
| | PHF | N-Acetyl Cysteine | 339.1 | 0.7 | $5.2 \times 10^5$ | 0.0002 |

Hydrogen sulfide ($H_2S$) is a gaseous transmitter in the blood that acts as a potent anti-oxidant, has anti-inflammatory activity and stimulates NO, thus a target for improving vascular health. In vitro data has shown the H2S activity and previous animal studies with the fullerene have shown benefits in aging.

Examples of the sulfur-containing compound that serves as the substrate for fullerenes includes, for example, different sulfur-containing amino acids including cysteine, homocysteine, methionine and N-acetyl cysteine. In work conducted during development of embodiments herein, it was shown that PLP (Vitamin B6, which is a co-factor for enzymatic production of $H_2S$) is not necessary for PHF to generate $H_2S$.

In certain embodiments, the fullerenes described herein are employed with carriers (e.g., particles or devices). Examples of particle matrix carriers include, for example, Polymers: PLGA, PLA, PCL, PEG, Chitosan, alginate, pluronics, lipids and Eudragit; Inorganic: Silica, silicon, titanium dioxide, ceria and amorphous carbon; Metals: Gold, silver and copper; and Eudragit polymers that are either time-dependent release or pH-sensitive and may be preferable for medical food, whereas silica may be preferable for topical application and PEG coated particles for intravenous administration.

The fullerenes described herein may be used to treat a subject in order to treat a disease or condition. The type of administration is not limited, and could be intravenous, intraocular, topical, etc. In some embodiments, the disease or condition is, for example, heart failure (HF), heart disease (HD), chronic kidney disease, Alzheimer's disease (AD) and peripheral artery disease (PAD).

In certain embodiments, cardiovascular disease (e.g., heart failure or chronic heart failure) is treated with the fullerenes described herein. In heart failure, it has been shown that hydrogen sulfide is inversely correlated to severity of disease and to poor prognosis. Cardiovascular is a brood classification of a disease area that has many different manifestations, including hypertension, dyslipedmia, chronic heart failure, stroke, acute heart failure, angina, atrial fibrillation and peripheral arterial disease. The total cardiovascular market was estimated at ~$145 billion in 2007, with the majority of the market being attributed to hypertension and dyslipidemia. While these segments have been well served, others such as chronic and acute heart failure remain largely symptomatically treated. The American Heart Association estimates the prevalence of heart failure in the U.S. is estimated near 6 million and analyst expected it to grow to 9 million by 2022. While the disease does occur in all ages, it is predominantly a disease of the elderly and a driver of the expansion due to the aging population. Heart failure the most common cause of hospitalization in the US and total treatment costs continue to rise each year. Heart failure is estimated to account for over $40 billion in total costs and results in almost ½ million deaths annually in the US alone.

Chronic heart failure is a condition in which the heart can not pump blood adequately and can arise from genetic defect, injury or disease. The inability to deliver blood efficiently to the body leads to shortness of breath, tiredness, and edema (build up of fluids), which further exasperates the shortness of breath and tiredness. The cardiac structural and functional dysfunction that is characterized in heart failure is often defined in terms of the left ventricle ejection fraction (LVEF). On the basis of ejection fraction (EF), heart failure can be classified as with reduced EF (HF-REF) or preserved EF (HF-PEF). Normal EF is usually considered to be above 50%. In patients with reduced EF, the left ventricle (LV) is unable to contract properly and ejects smaller fraction of blood than normal. Patients with preserved EF have normal LVEF but have LV diastolic dysfunction. Usually patients with preserved EF have an increase in LV wall thickness and increased left atrial size.

The drugs available for treating chronic heart failure are largely enzyme inhibitors or receptor agonists or antagonists which may improve outcome but do not treat the underlying disease. In contrast, hydrogen sulfide prodrugs have been shown in animal studies to improve ventricular function, including ejection fraction and actually reverse disease progression. Although the sales in the over-all cardiovascular markets are declining as the major anti-hypertensive drugs and anti-dyslipidemia drugs are coming off patent, the heart failure market remains exceptionally strong and is predictive to increase significantly over time.

In certain embodiments, fullerenes are used to generate H2S in vivo to treat alcoholism, opioid withdrawal, or heroin withdrawal. In certain embodiments, fullerenes are used to generate H2S in vivo to treat Alzheimer's disease or chronic fatigue syndrome. In certain embodiments, fullerenes are used to generate H2S in vivo to improve social interaction or treat abnormal behavior. In certain embodiments, fullerenes are used to generate H2S in vivo to treat ulcers, airway inflammation, diabetes, obesity, and for causing weight loss. In certain embodiments, fullerenes are used to generate H2S in vivo to treat epilepsy, erectile dysfunction (ED), depression, anxiety, Huntington's disease, high blood pressure, hypertension, colitis, sleep apnea, and Parkinson's disease (PD). In certain embodiments, fullerenes are used to generate H2S in vivo to reduce the severity of neurological injury or prevent stroke. In certain embodiments, fullerenes are used to generate H2S in vivo to treat pulmonary hypertension or prevent renal fibrosis. In certain embodiments, fullerenes are used to generate H2S in vivo to treat gout, a rheumatic disease, skin conditions (including skin disease or cosmetic condition), ocular diseases and osteoarthritis. In some embodiments, fullerenes are used to treat conditions such as hyperhomocysteinemia, homocystinuria, cystinuria, and cystine stones.

In certain embodiments, the fullerenes described herein is applied locally, such as to the skin, eye, or joint of a subject. For example, for treating and preventing a skin condition (skin disease or cosmetic skin condition) a local application, such as a dermal application, the application is performed at a defined part of the skin (e.g. to a skin area, wherein the skin condition occurs or is expected to occur). The local application may include treating a skin area superficially, intradermally or subcutaneously, i.e. by injection under the skin area of issue. In regard to treating ocular disease, a local application to the ocular tissues may be employed. The local application may include applying the compound for use according to the invention on the ocular surface, e.g. in the form of eye drops, or by injection into the eye. The compound for use according to the invention may be administered as vitreous body substitute or as intraocular implant. In certain embodiments, the fullerenes described herein are used to treat osteoarthritis with a local application to a joint. The compound for use according to the invention may be administered as viscosupplement. A viscosupplement is injected as a gel into the joint of issue, e.g. knee, referred to as intraarticular injection.

In certain embodiments, the fullerene compositions according to the present technology comprises or consists of a pharmaceutically acceptable carrier, diluent, or excipient (including combinations thereof). Acceptable carriers or diluents for therapeutic use are well known in the pharmaceutical art and are described, for example, in Remington's Pharmaceutical Sciences, Mack Publishing Co. (A. R. Gennaro edit. 1985). The choice of pharmaceutical carrier, excipient, or diluent is selected with regard to the intended route of administration and standard pharmaceutical practice. The pharmaceutical comprise as, or in addition to, the carrier, excipient, or diluent any suitable binder(s), lubricant (s), suspending agent(s), coating agent(s), and/or solubilizing agent(s). This pharmaceutical composition will desirably be provided in a sterile form. It may be provided in unit dosage form and will generally be provided in a sealed container. A plurality of unit dosage forms may be provided.

Pharmaceutical compositions within the scope of the present technology may include one or more of the following: preserving agents, solubilizing agents, stabilizing agents, wetting agents, emulsifiers, sweeteners, colorants, flavoring agents, odorants, and/or salts. Compounds of the present technology may themselves be provided in the form of a pharmaceutically acceptable salt. In addition, embodiments may comprise buffers, coating agents, antioxidants, suspending agents, adjuvants, excipients, and/or diluents. Examples of preservatives include sodium benzoate, sorbic acid, and esters of p-hydroxybenzoic acid.

They may also contain other therapeutically active agents in addition to compounds of the present technology. Where two or more therapeutic agents are used they may be administered separately (e.g., at different times and/or via different routes) and therefore do not always need to be present in a single composition. Thus, combination therapy is within the scope of the present technology.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, via the penis, vaginal, epidural, sublingual. It is to be understood that not all of the agent need be administered by the same route. Likewise, if the composition comprises more than one active component, then those components may be administered by different routes.

If the fullerenes described herein is administered parenterally, then examples of such administration include one or more of: intravenously, intra-arterially, intraperitoneally, intrathecally, intraventricularly, intraurethrally, intrastemally, intracranially, intramuscularly, or subcutaneously administering the agent; and/or by using infusion techniques.

In some embodiments, pharmaceutical compositions adapted for oral administration are provided as capsules or tablets; as powders or granules; as solutions, food product, syrups or suspensions (in aqueous or non-aqueous liquids); as edible foams or whips; or as emulsions. Tablets or hard gelatin capsules may comprise lactose, maize starch or derivatives thereof, stearic acid or salts thereof. Soft gelatin capsules may comprise vegetable oils, waxes, fats, semi-solid, or liquid polyols etc. Solutions and syrups may comprise water, polyols and sugars. For the preparation of suspensions, oils (e.g., vegetable oils) may be used to provide oil-in-water or water-in-oil suspensions. An active agent intended for oral administration may be coated with or admixed with a material that delays disintegration and/or absorption of the active agent in the gastrointestinal tract (e.g., glyceryl monostearate or glyceryl distearate may be used). Thus, the sustained release of an active agent may be achieved over many hours and, if necessary, the active agent can be protected from being degraded within the stomach. Pharmaceutical compositions for oral administration may be formulated to facilitate release of an active agent at a particular gastrointestinal location due to specific pH or enzymatic conditions.

Alternatively, the fullerenes described herein may be applied topically in the form of a gel, hydrogel, lotion, solution, cream, ointment or dusting powder. The agent of the present technology may also be dermally or transdermally administered, for example, by the use of a skin patch. For application topically to the skin, the agent of the present technology can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water. If the fullerenes are administered parenterally, then examples of such administration include one or more of: intravenously, intra-arterially, intraperitoneally, intrathecally, intraventricularly, intraurethrally, intrasternally, intracranially, intramuscularly or subcutaneously administering the agent; and/or by using infusion techniques.

Typically, a physician will determine the actual dosage of the fullerenes which will be most suitable for an individual subject. The specific dose level and frequency of dosage for any particular patient may be varied and will depend upon a variety of factors including the activity of the specific compound employed; the metabolic stability and length of action of that compound; the age, body weight, general health, sex, diet, mode and time of administration; rate of excretion; drug combination; the severity of the particular condition; and the individual undergoing therapy. The agent and/or the pharmaceutical composition of the present technology may be administered in accordance with a regimen of from 1 to 10 times per day, such as once or twice per day. For oral and parenteral administration to human patients, the daily dosage level of the agent may be in single or divided doses.

"Therapeutically effective amount" refers to the amount of the fullerenes describe herein that is effective to achieve its intended purpose (e.g., treating symptoms of an inflammatory disease or other disease or condition described herein). The methods described herein may employ a daily therapeutically effective amount. While individual patient needs may vary, determination of optimal ranges for effective amounts of the compounds related to the technology is within the skill of the art. Generally, the dosage regimen for treating a condition with the compounds and/or compositions of this technology is selected in accordance with a variety of factors, including the type, age, weight, sex, diet and medical condition of the patient; the severity of the dysfunction; the route of administration; pharmacological considerations such as the activity, efficacy, pharmacokinetic and toxicology profiles of the particular compound used; whether a drug delivery system is used; and whether the compound is administered as part of a drug combination and can be adjusted by one skilled in the art. Thus, the dosage regimen actually employed may vary widely and therefore may deviate from the exemplary dosage regimens set forth herein.

In certain embodiments, the particular molecular structure of a given PHF is varied depending on the type of substrate, temperature, ionic strength, pH and the desired catalysis rate. For example, in general, if higher substrate affinity is desired, then the number of ionic functional groups (e.g., (OH), 0 or NH) is increased, and if higher catalytic rate is desired, then the number of functional groups is decreased. Further, in work conducted during the development of embodiments herein, it was observed that addition of thiol groups or disulfide groups can significantly increase catalytic activity.

EXAMPLES

Example 1

H2S is produced from cysteine by the enzymes cystathionine β-synthase (CBS) and cystathionine γ-lyase (CGL) in the body. It was discovered that: 1) PHF catalytically produces H2S from cysteine and homocysteine (FIG. 1A), and 2) PHF enhances endogenous production of H2S (FIG. 1B). Further, the catalytic activity depends on the molecular structure of PHF (FIG. 1A). FIG. 1 shows that polyhydroxy fullerenes (PHF) catalytically produces hydrogen sulfide ($H_2S$). A) PHF stimulates H2S production catalytically in a cell-free chemical reaction involving cysteine and vitamin B6 (PLP) as determined by the lead acetate/lead sulfide method. B) PHF dose-dependently boosts endogenous H2S production in human liver derived (HepG2) cells as determined by an increase in the fluorescence of an H2S detecting chemical probe. Additionally, FIG. 1A shows that polyhydroxy fullerenes (PHF) catalytically produces hydrogen sulfide ($H_2S$) with different PHF formulations MER, SJJR, and JR stimulate H2S production catalytically in a cell free chemical reaction involving cysteine and vitamin B6 as determined by the lead acetate/lead sulfide method (left image) and quantified in the graph to the right. * indicates significant difference ($p<0.05$) compared to reaction (Rxn) mix alone, and FIG. 1B shows PHF dose-dependently boosts endogenous H2S production in human liver derived (HepG2) cells as determined by an increase in the fluorescence of an H2S detecting chemical probe. * indicates significant difference ($p<0.05$) compared to 0 PHF control group. For MER, SJJR, and JR, used in this example, we used X-ray Photoelectron Spectroscopy (XPS) to estimate their molecular structures. The proposed structures are: i) MER: $C_{60}(OH)_{11}O_8Na_7$ (note that the manufacturer says that their PHF is $C_{60}(OH)_{24}$ and our characterization shows it different); ii) SJJR: $C_{60}(OH)_{10}O_6Na_4$; and iii) JR: $C_{60}(OH)_{23}O_5Na_4$.

Further work was conducted as follows with regard to the catalytic production of H2S by PHFs. PHF (SJJR; 10 mg/mL) was added to a mixture of L-cysteine (10 mM) and pyridoxal L-phosphate (PLP; 1 mM) in a 96-well plate and then covered with a blotting paper saturated with lead acetate. After 24 hours, the lead acetate paper was removed and scanned. The lead sulfide dots were analyzed for average integrated density using ImageJ. After every 24 hours, the wells were replenished with L-cysteine (10 mM) and covered with the lead acetate paper and the lead sulfide dots were analyzed. FIG. 2 shows that the H2S production does not decrease with time showing that PHF is not consumed and hence, PHF is a catalyst.

Example 2

Catalytic Activity of PHFs

For the experimental work described below, PHFs with general formula of a) C60(OH)tOyMzM'z' and b) C60(OH)t(SH)uOyMz or C60(OH)t(S)uOyMz, were employed. Examples of a) include: $C_{60}(OH)_9O_7Na_6$; $C_{60}(OH)_{11}O_8Na_5$; $C_{60}(OH)_{11}O_{12}Na_8$; and $C_{60}(OH)_{11}O_{20}Na_{10}K_6$;

Lead acetate assay: The kinetics and catalysis coefficients for PHF catalyzed $H_2S$ production were determined using lead acetate assay (PbA/PbS assay) as generally described in Hine and Mitchell, "Endpoint and Kinetic Measurement of Hydrogen Sulfide Production Capacity in Tissue Extracts" Bio-Protocol, 7 (13), e2382, 2017). Briefly: Reaction mixtures (150 μL/well) containing PHF or enzyme (CGL), enzyme co-factor (PLP) and substrate (e.g., cysteine) were tested in 96-well plates Immediately after addition of catalyst, 96-well plates were covered with lead acetate saturated paper and placed inside a 37° C. cell culture incubator. At a predetermined time point, the lead acetate paper was removed and scanned, and the lead sulfide dots analyzed with ImageJ using the IntDen function. A calibration curve was prepared with different concentrations of sodium hydrosulfide plotted against the integrated density obtained on lead acetate/lead sulfide paper. The presence of pyruvic acid after reaction was confirmed in a preliminary experiment by liquid chromatography—mass spectroscopy.

Figure 5:
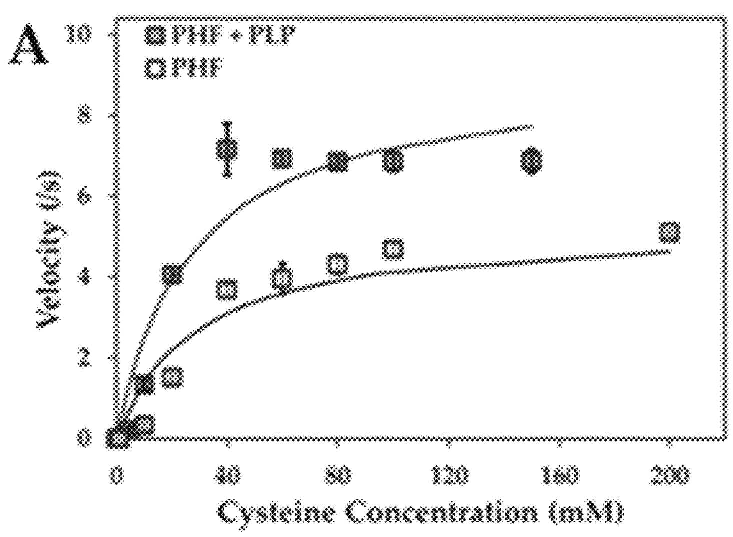
FIG. 5: Steady-state kinetics of H2S production. Michaelis-Menten kinetics for PHF-catalyzed H2S production with: Panel A) cysteine, Panel B) homocysteine and Panel C) n-acetyl cysteine as substrates. No H2S production was observed with methionine as substrate. PLP (when added) initial concentration was 1 mM; PHF concentration was 10 mg/mL.
Figure 5:
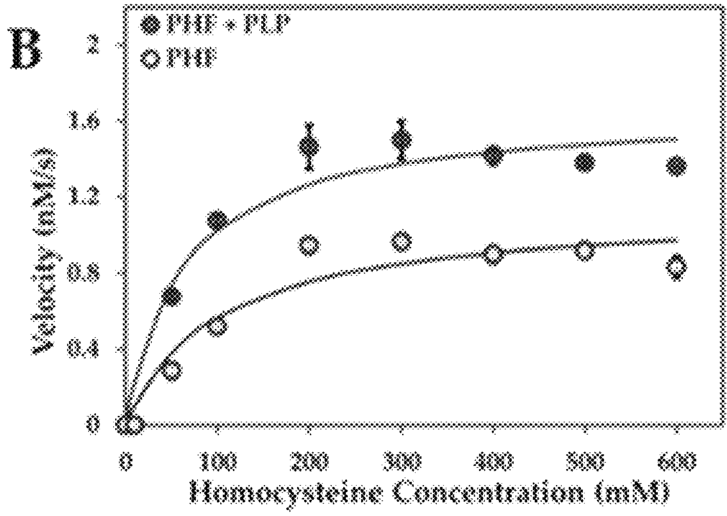
Figure 5:
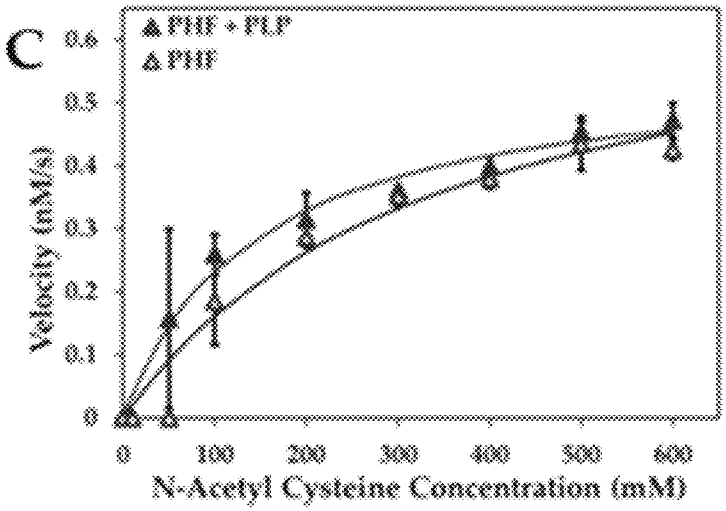
Figure 6:
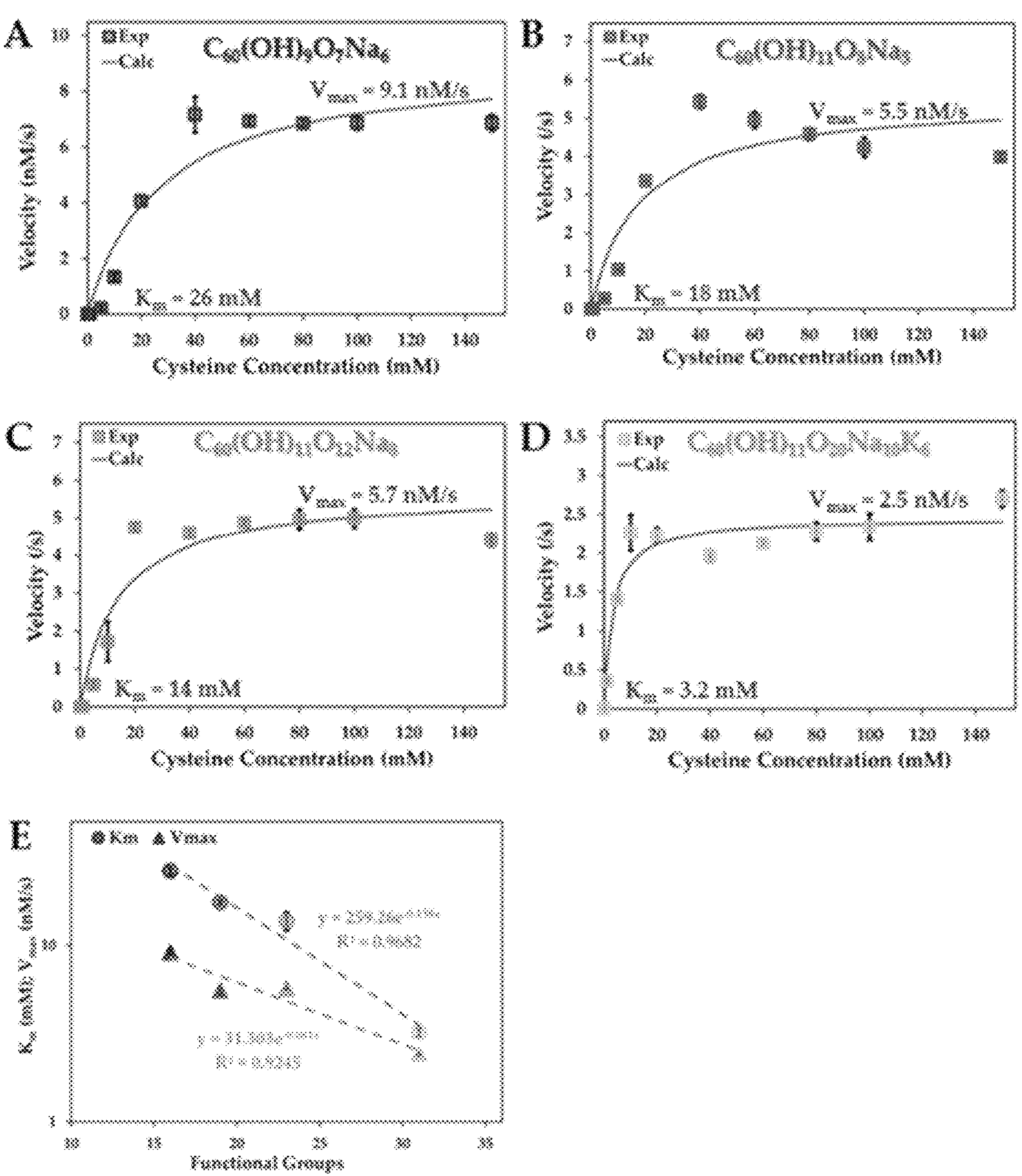
FIG. 6: Effect of PHF structure on H2S production kinetics with cysteine as substrate. Michaelis-Menten kinetics for H2S production in presence of PLP with different molecular structures of PHF: A) $C_{60}(OH)_9O_7Na_6$, B) $C_{60}(OH)_{11}O_8Na_5$, C) $C_{60}(OH)_{11}O_{12}Na_8$ and D) $C_{60}(OH)_{11}O_{20}Na_{10}K_6$. E) Correlation of Km and Vmax with number of PHF functional groups. PLP initial concentration was 1 mM; PHF concentration was 10 mg/mL.

To determine the steady-state kinetic parameters experiments were carried out with different initial substrate concentrations. The initial (linear) slope from the graph of H2S concentration versus time at each substrate concentration was used to determine the reaction velocity, which was plotted against initial cysteine concentrations to obtain Michaelis-Menten curves (FIGS. 5 and 6). Least squares non-linear fitting was used to determine values of Km and Vmax from the equation $v=Vmax\,[S]/(Km+[S])$.

Figures 4A, 4B:
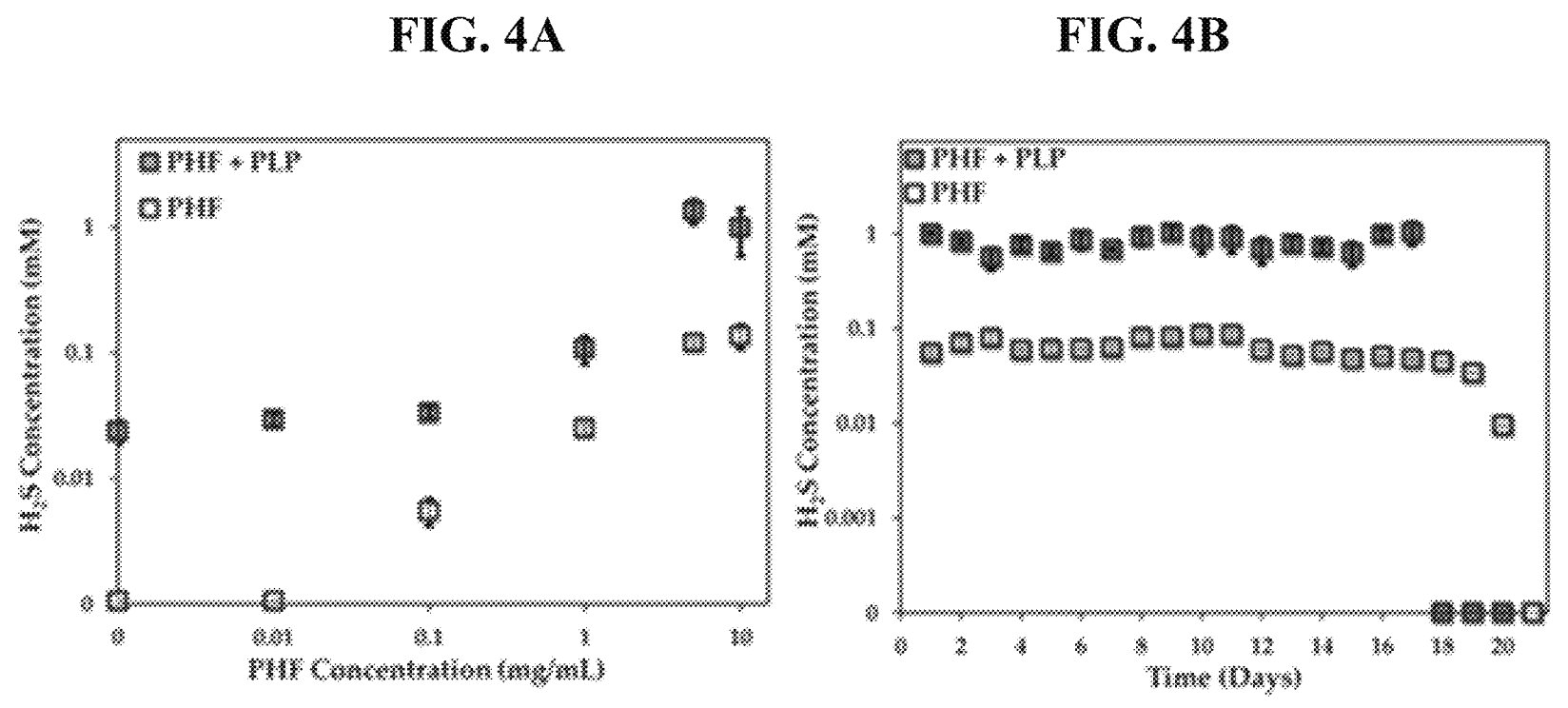

Cysteine, by itself under physiological conditions, does not breakdown to produce $H_2S$ (FIG. 4*a*). PLP reacts with cysteine slowly to produce $H_2S$ (0.024 mM in 24 hours). Addition of PHF to the cysteine-PLP mixture increased $H_2S$ production in a concentration dependent manner. Interestingly, H2S production with PHF was observed even in the absence of PLP. $H_2S$ production increased with addition of PLP at every concentration of PHF tested. Since $H_2S$ generation in both the presence and absence of PLP was highest at 10 mg/mL PHF, further experiments were carried out at this concentration.

In order to investigate the role of PHF in $H_2S$ production with cysteine, a multi-day experiment was carried out in which cysteine was added every 24 hours for 17 days. In case PHF is a reactant, the $H_2S$ production should decrease with repeated cysteine addition until all PHF is consumed. FIG. 4*b* shows that PHF is a catalyst as the amount of $H_2S$ produced does not decrease with repeated addition of substrate in presence or absence of PLP. To confirm that the steady $H_2S$ production was not due to unreacted cysteine, after 17 days the cysteine addition was stopped and $H_2S$ was measured every 24 hours for 4 more days. In presence of PLP all cysteine is reacted in 24 hours and no $H_2S$ was detected on days 18-21. In absence of PLP, $H_2S$ production decayed with time and no $H_2S$ was detected on day 21.

Figures 4C, 4D:
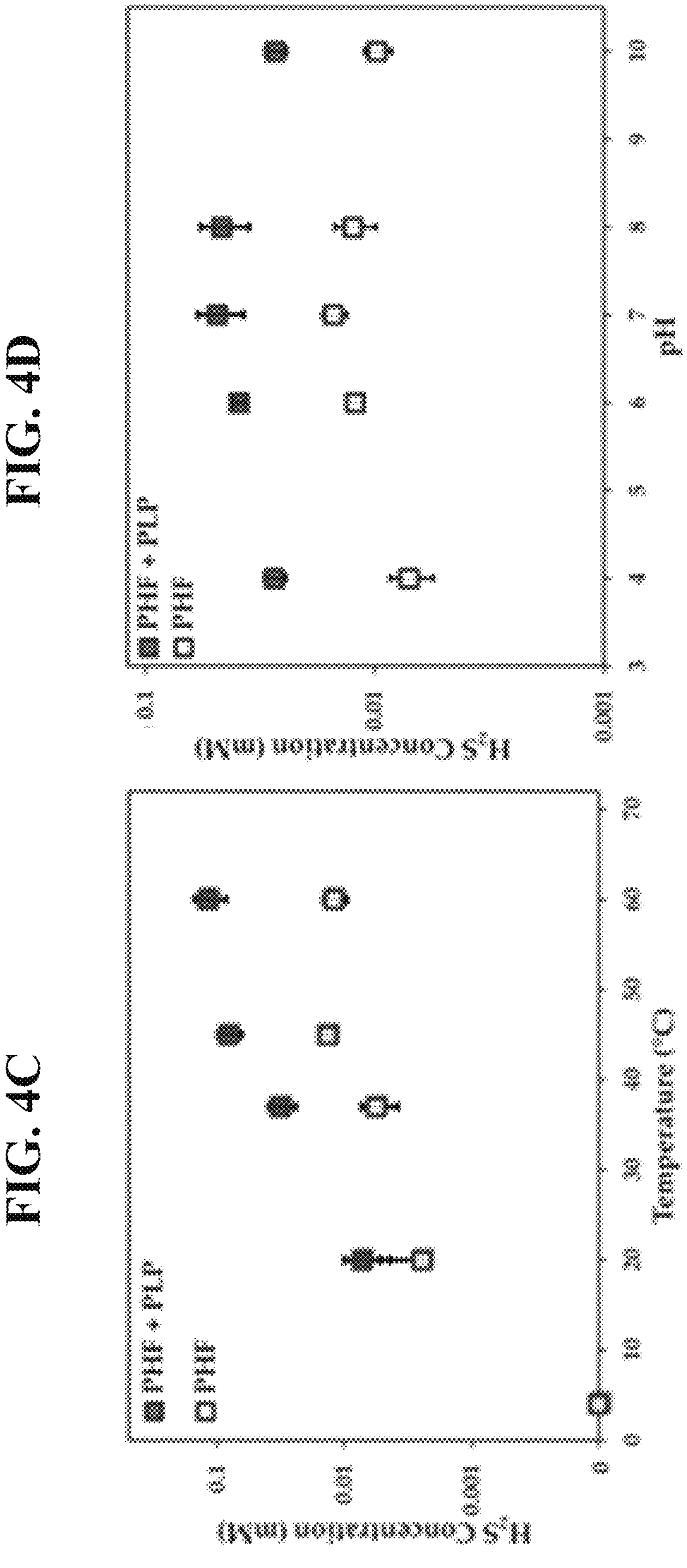

The catalytic activity of PHF is dependent on pH and temperature. Experiments at different pH were carried out in deionized water instead of PBS (FIG. 4*c*). PHF catalytically produced $H_2S$ at all pH tested with maximum production around pH 7. Addition of PLP enhanced the amount of H2S produced without affecting the trend with pH.

The effect of temperature was determined with reaction taking place in PBS to simulate physiological conditions (FIG. 4*d*). No H2S was produced at 4° C. in the presence or absence of PLP for both PHF and CGL. At room temperature, CGL produced $H_2S$ only in presence of PLP. However, with PHF, $H_2S$ produced was very low and there was no significant difference between $H_2S$ production in presence or absence of PLP. $H_2S$ production increased with temperature and the amount of $H_2S$ produced was higher in presence of PLP than in absence of PLP at 37, 45 and 60° C.

In presence of PLP, there is a slow increase in reaction velocity at lower cysteine concentrations, suggesting competition of substrate binding with PLP and PHF, as shown in FIG. 5. The maximum reaction velocity obtained by nonlinear curve fitting is 15.34 (nM)/s and the Michaelis constant ($K_M$) is 35.3 mM. In absence of PLP, reaction velocity increases with cysteine concentration and reaches plateau, which is typical for a catalyst. The maximum reaction velocity with PLP (15.34 nM/s) is higher than in absence of PLP (5.92 nM/s). The K M in absence of PLP (27.3 mM) is lower than in presence of PLP (35.3 mM) corroborating the competitive binding effect.

Interestingly, PHF was able to catalyze breakdown of C—SH bonds in homocysteine and n-acetyl cysteine in presence and absence of PLP. The K M values for homocysteine were higher than cysteine and were highest for n-acetyl cysteine (FIG. 5C). Unlike cysteine, the $K_M$ values in absence of PLP were higher than with PLP, suggesting that PLP does not bind strongly with homocysteine or n-acetyl cysteine. Similar to $K_M$, the $V_{Max}$ for homocysteine was smaller than cysteine and smallest for n-acetyl cysteine. No $H_2S$ production was observed for methionine as substrate in presence or absence of PLP. This suggests PHF may only cleave terminal thiols.

Polyhydroxy fullerenes can be synthesized with different number of hydroxyl and hemi-ketal groups attached to fullerene cage, which can be determined with XPS C1s spectrum as mono-oxygenated and di-oxygenated carbon, respectively. Different PHF structures were synthesized and their $K_M$ and $V_{Max}$ were determined (FIG. 6*a-d*). The higher the total number of functional groups greater is the production of $H_2S$. Further, with increase in functional groups $K_M$ and $V_{Max}$ decreases (FIG. 4*e*). The $K_M$ value for PHF with highest number of functional group tested (31) was similar to CGL enzyme, however, the $V_{Max}$ for PHF31 was 10 fold higher than CGL enzyme. These results suggest that PHF structure can be modified to obtain desired $K_M$ and $V_{Max}$ values.

Figure 7:
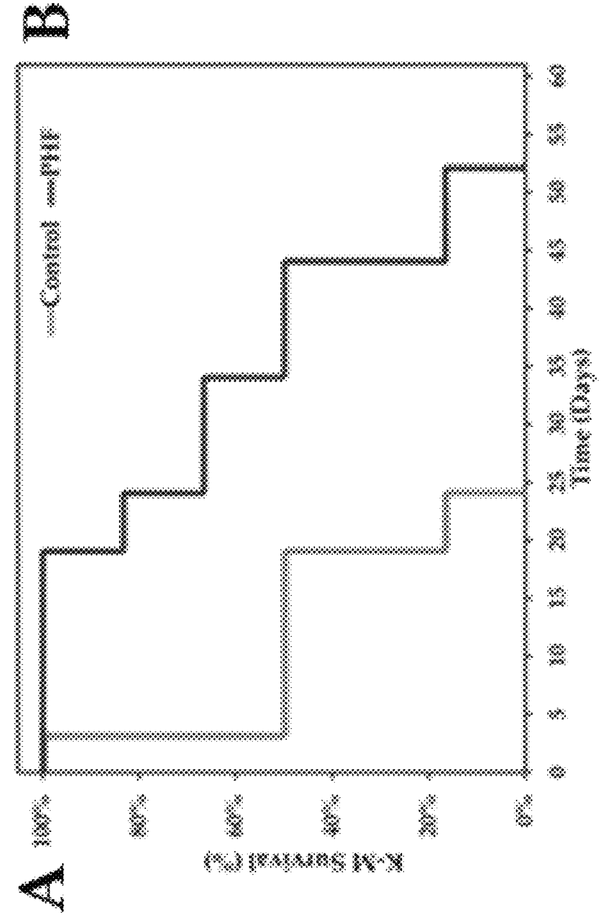
FIG. 7: Application of PHF to rescue CGL deficiency. A) Kaplan-Meir survival curve for female CGL knockout mice on high-fat diet and i.p. injections of saline or PHF (200 μL) three times a week. The median survivals for control and PHF were 11 and 39 days, respectively. The P value from Log-rank (Mantel-Cox) test was 0.0061. (n=6). B) The color of feces in PHF treated mice were dark brown due to PHF color.
Figure 7:
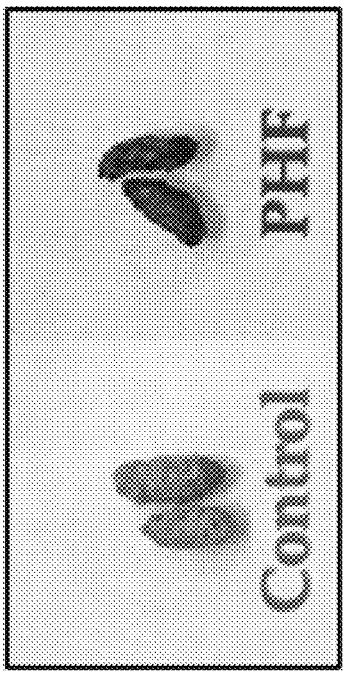

In vivo experiments were carried out with 12 female CGL knockout mice with results shown in FIG. 7. The mice were fed with high-fat diet amended with higher methionine concentration. The first group of mice (n=6) received intraperitoneal injections of PHF (200 μL) three times a week. The second group of mice (n=6) were injected with PBS. The $H_2S$ production from CGL enzyme is critical for fat accumulation in adipocytes (fat cells). The CGL knockout mice fed with high fat diet have higher lipid levels in blood (due to their inability to accumulate lipids into fat cells), which is toxic and fatal. The median survival of control (PBS) mice was 11 days (FIG. 7A). In contrast, PHF catalytically produces $H_2S$ that can help in lipid accumulation and increase the median survival to 39 days. PHF's bioavailability is demonstrated by change in color of feces of PHF-injected mice vs control mice (FIG. 7B).

Figure 8:
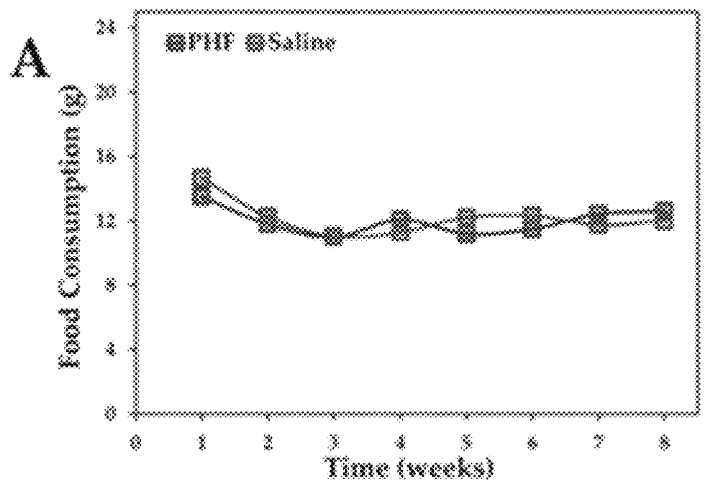
FIG. 8: Application of PHF to treat metabolic disease. Panel A) The food consumption in saline and PHF treated mice is similar over 8 weeks. Panel B) The saline treated mice have gained more body weight than PHF-treated mice even with similar food consumption. Panel C) The glucose tolerance of PHF-treated mice is higher, whereas saline-treated mice show symptoms of diabetes. Female wild-type mice were fed with high fat/high salt diet and injected with 100 μL of PHF (1 mg/mL) or saline three times a week for 8 weeks. (n=5).
Figure 8:
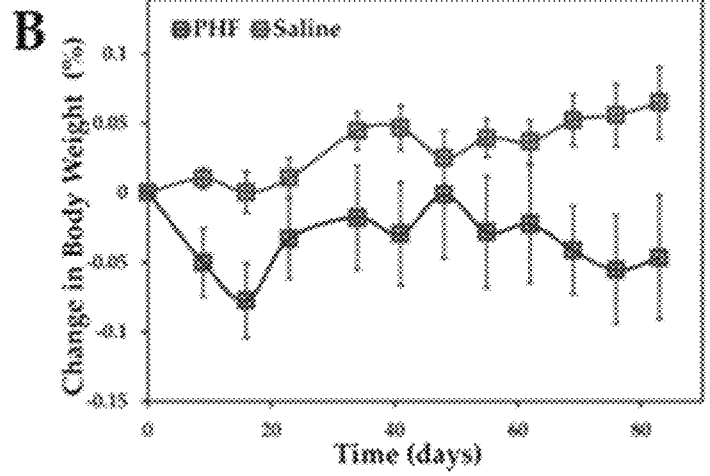
Figure 8:
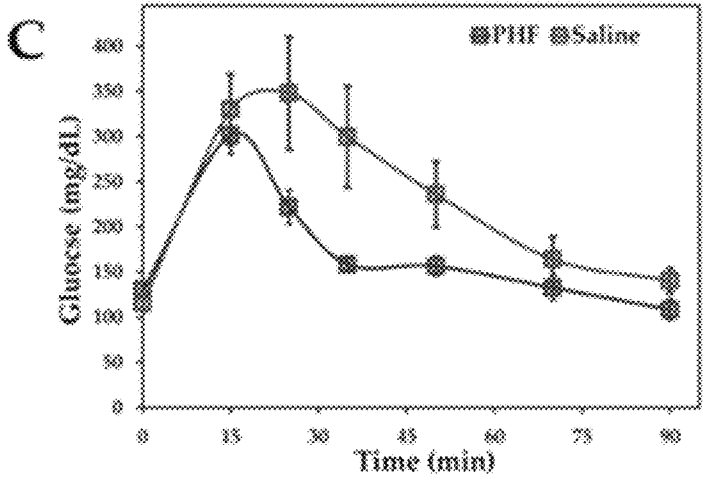

In vivo experiments were carried out with 10 female C57B1/6 mice. The mice were fed with high-fat/high salt (HFHS) diet. The HFHS diet is expected to induce obesity in mice and reduce their glucose tolerance. The first group of mice (n=5) received intraperitoneal injections of PHF (100 μL) three times a week. The second group of mice (n=5) were injected with PBS. At the beginning of the experiment, 100 g of HFHS food was added to each cage. Every week, the amount remaining was measured and replenished to a total weight of 100 g. FIG. 8*a* shows that there was no difference in the amount of food consumed by PHF-treated or control mice over 8 weeks of experiments. Interestingly, the percent change in body weight for PHF-treated mice was lower than control mice (FIG. 8B). Most importantly, glucose tolerance test suggested that PHF-treated mice have normal glucose tolerance compared to control mice that exhibit diabetic symptoms (FIG. 8C).

Figure 9:
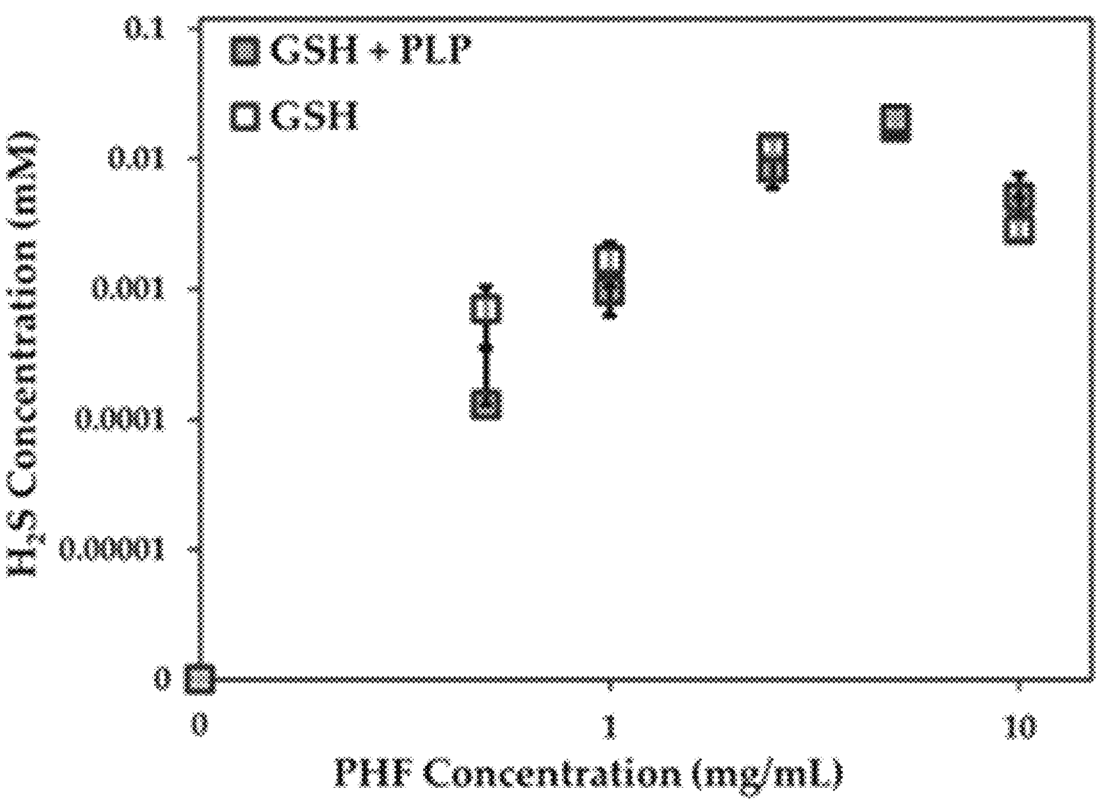
FIG. 9: PHF catalytically cleaves C—SH bond in a peptide. Effect of PHF concentration on H2S production from glutathione (initial concentration of 10 mM) in the presence or absence of pyridoxal-5'-phosphate (PLP). Glutathione is a 3 amino acid peptide with cysteine in center. PLP does not enhance PHF's catalytic activity.

PHF can cleave C—SH bond even when cysteine is part of a peptide (FIG. 9). However, the $H_2S$ production volume is 100 times much lower than for free cysteine at similar concentrations.

REFERENCES

Alves et al., (2011), Eur J Pharmacol 654, 60-67.
Blackstone et al., (2005), Science 308, 518.
Elrod et al., (2007), Proc Natl Acad Sci USA 104, 15560-15565.
Giuliani et al., (2013), Neurobiol Learn Mem 104, 82-91.
Hine et al. (2015), Cell 160, 132-144.
Hine et al. (2017), Cell Metab 25, 1320-1333 e1325.
Huang et al. (2015), Nitric Oxide 46, 192-203.
Jha et al., (2008), Am J Physiol Heart Circ Physiol 295, H801-806.
Kovacic et al., (2012), J Card Fail 18, 541-548.
Liu et al. (2014), Cell Stem Cell 15, 66-78.
Paul et al., (2014), Nature 509, 96-100.
Polhemus et al., (2015), Cardiovasc Ther 33, 216-226.
Sponholz et al. (2016), Eur J Hum Genet 24, 1041-1048.
Suzuki et al. (2011), Proc Natl Acad Sci USA 108, 13829-13834.
Szabo, C. (2012), Antioxid Redox Signal 17, 68-80.
Xue et al. (2013), Antioxid Redox Signal 19, 5-23.
Yang et al. (2008), Science 322, 587-590.
Zhang et al., (2013), Mol Cell Biol 33, 1104-1113.
Zhao et al., (2001), The EMBO journal 20, 6008-6016.
Zhu et al., (2008), Biochemistry 47, 6226-6232.

All publications and patents mentioned in the above specification are herein incorporated by reference in their entirety for all purposes. Various modifications and variations of the described compositions, methods, and uses of the technology will be apparent to those skilled in the art without departing from the scope and spirit of the technology as described. Although the technology has been described in connection with specific exemplary embodiments, it should be understood that the technology as claimed should not be unduly limited to such specific embodiments. Indeed, various modifications of the described modes for carrying out the technology that are obvious to those skilled in pharmacology, biochemistry, medical science, or related fields are intended to be within the scope of the following claims.

We claim:

1. A method comprising: contacting a thiol-containing compound with a composition comprising C60 polyhydroxy-fullerenes in vitro such that H2S is generated.

2. The method of claim 1, further comprising capturing at least some of said H2S that is generated.

* * * * *